United States Patent [19]

Owen et al.

[11] Patent Number: 4,912,240
[45] Date of Patent: Mar. 27, 1990

[54] ORGANOFUNCTIONAL BETAINE MODIFIED SILOXANES

[75] Inventors: Michael J. Owen; Steven A. Snow, both of Midland, Mich.

[73] Assignee: Dow Corning Corporation, Midland, Mich.

[21] Appl. No.: 227,391

[22] Filed: Aug. 1, 1988

[51] Int. Cl.$^4$ .............................................. C07F 7/10
[52] U.S. Cl. .................................................... 556/418
[58] Field of Search ......................................... 556/418

[56] References Cited
U.S. PATENT DOCUMENTS 4,342,742  8/1982  Sebag et al. .................... 556/418 X

*Primary Examiner*—Paul F. Shaver
*Attorney, Agent, or Firm*—Marc C. Pawl

[57] ABSTRACT

The invention relates to novel compositions of organofunctional betaine modified siloxanes having the general formula:

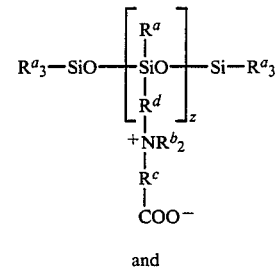

and

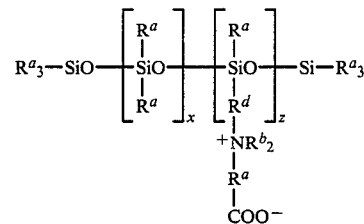

wherein each $R^a$ and $R^b$ are lower alkyl groups, $R^c$ and $R^d$ are lower alkylene groups, x ranges from 1–4, and z ranges from 1–4. The compositions of the invention exhibit surfactant properties in that they are effective in lowering the surface tension of water. The invention also regards the process by which these modified siloxanes are made.

5 Claims, No Drawings

ORGANOFUNCTIONAL BETAINE MODIFIED SILOXANES

BACKGROUND OF THE INVENTION

This invention relates to new compositions of matter which are broadly described as organofunctional betaine modified siloxanes. These compositions exhibit high aqueous surface activity in that they are effective in lowering the surface tension of water.

Previously, other organobetaine modified siloxane surfactants have been made with structures different than the present invention. These include the compositions disclosed in U.S. Pat. Nos. 4,609,750 and 4,654,161 in which the organobetaine substituents on the siloxane contain multiple nitrogens.

SUMMARY OF THE INVENTION

The present invention relates to organofunctional betaine modified siloxanes which have the general formulas:

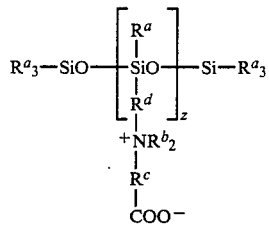

and

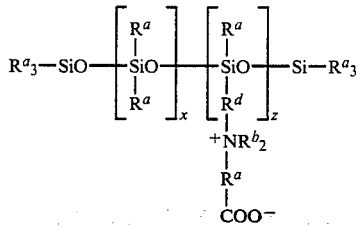

where $R^a$ is a lower alkyl group, $R^b$ is hydrogen or a lower alkyl group, $R^c$ and $R^d$ are lower alkylene groups, x ranges from 1-10, and z ranges from 1-4.

DETAILED DESCRIPTION OF THE INVENTION

The compositions of the invention are organofunctional betaine modified siloxanes having general formulas selected from the group consisting of:

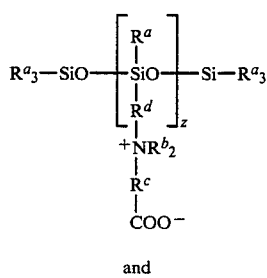

and

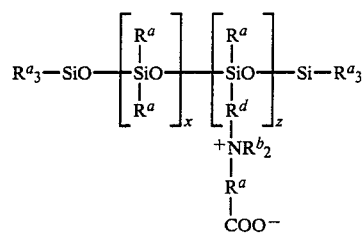

wherein each $R^a$ represents a lower alkyl group, each $R^b$ is selected from the group consisting of hydrogen and a lower alkyl group, and $R^c$ and $R^d$ are lower alkylene groups. Specifically, each $R^a$ represents an alkyl group of from 1-6 carbons, each $R^b$ is selected from the group consisting of hydrogen and an alkyl group of from 1-18 carbons, $R^c$ represents an alkylene group of from 1-10 carbons, $R^d$ represents an alkylene group of from 2-8 carbons, x ranges from 1-10, and z ranges from 1-4. In other embodiments of the invention, it is preferred that each $R^a$ represent an alkyl group of from 1-4 carbons, with methyl being the most preferred, each $R_b$ is preferred to be an alkyl group of 1-6 carbons, with methyl being the most preferred, $R^c$ is preferred to represent an alkylene group of 1-2 carbons, with methylene being the most preferred, $R^d$ is preferred to be propylene, and x is preferred to represent 1-4.

The compositions of the invention are obtained through the reaction of an aminofunctional siloxane with a halogenated salt of a carboxylic acid as represented below:

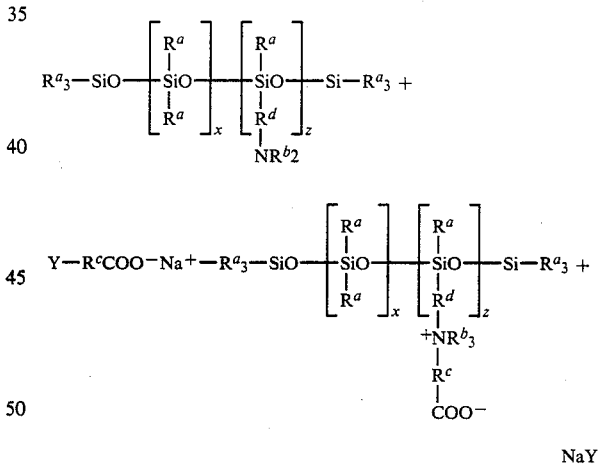

wherein $R^a$, $R^b$, $R_c$, $R_d$, x, and z are as defined above. In a preferred embodiment of the process, the carboxylic acid is acetic acid. Y is a halogen and preferably a member of the group consisting of Cl, Br and I.

EXAMPLE

An amount of methylfunctional betaine modified siloxane was prepared by loading a 100 ml three-necked round bottom flask with 13.1 g of the chlorinated salt of acetic acid (ClCH$_2$COONa) in 35 g of isopropanol. The flask was equipped with a magnetic stirring bar, condenser, N$_2$ gas inlet and dropping funnel. While being stirred under a nitrogen atmosphere, the mixture was heated to reflux, then 34.6 g of methyl aminofunctional siloxane Me$_3$-SiO-SiO(Me)-{(CH$_2$)$_3$-NMe$_2$}-Si(Me)$_3$ in 35 g isopropanol was added dropwise to the flask. Heating of the contents at reflux was continued for 24 hours. Subsequently, the volatile solvent was stripped off under vacuum at 100° C. The solid material remaining was dissolved in a mixture of methanol and isopropanol, filtered and again stripped of solvent. The recovered solids were washed with toluene and acetone, then again dissolved in isopropanol, reprecipitated by the addition of acetone and dried under a vacuum at 100° C. Elemental analysis of the material confirmed the formation of methyl substituted betainefunctional siloxane of the invention:

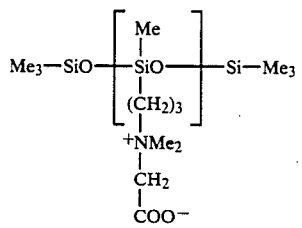

The process for producing the composition of the invention may be varied without substantially affecting the quality and volume of the yield of the reaction. While the inventors suggest the use of $N_2$ gas as the atmosphere of the reaction container, any inert gas will work well. The purpose of the inert atmosphere is to avoid the presence of moisture in the reaction container as the contents of the container are hygroscopic and the presence of water may adversely affect the reaction system. Furthermore, any alcoholic solvent of from $C_1$-$C_6$ is suitable as a solvent for the reaction system as long as the alcohol is capable of dissolving the reactants, especially the halogenated acetic acid.

Testing of methyl substituted betainefunctional siloxanes of the invention revealed the ability of the materials to reduce the equilibrium surface tension of water, therefore indicating utility as surface active agents.

What is claimed is:

1. Organofunctional betaine modified siloxanes selected from the group consisting of:

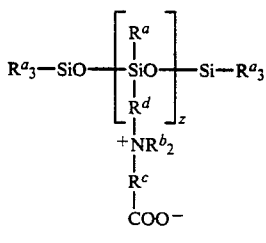

and

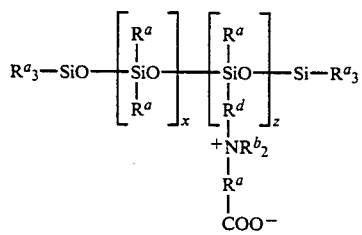

wherein each $R^a$ represents a lower alkyl group, each $R^b$ is selected from the group consisting of hydrogen and a lower alkyl group, $R^c$ and $R^d$ are lower alkylene groups, x ranges from 1-10, and z ranges from 1-4.

2. Organofunctional betaine modified siloxanes as claimed in claim 1, wherein each $R^a$ represents a lower alkyl group further defined as comprising from 1-6 carbons, each $R^b$ is selected from the group consisting of hydrogen and a lower alkyl group, wherein said lower alkyl group is further defined as comprising from 1-18 carbons, $R^c$ represents lower alkylene group further defined as comprising from 1-10 carbons, and $R^d$ represents a lower alkylene group further defined as comprising from 2-8 carbons.

3. Organofunctional betaine modified siloxanes as claimed in claim 2, wherein each $R^a$ represents an alkyl group of from 1-4 carbons, each $R^b$ represents an alkyl group of from 1-6 carbons, and x ranges from 1-4.

4. Organofunctional betaine modified siloxanes as claimed in claim 3, wherein each $R^a$ and $R^b$ are methyl, $R^c$ is methylene and $R^d$ is propylene.

5. A method of preparing organofunctional betaine modified siloxanes having a general formula selected from the group consisting of:

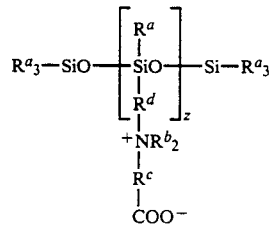

and

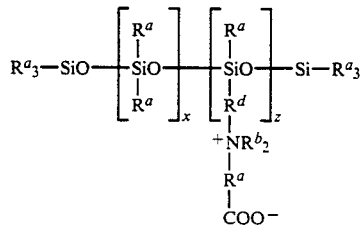

wherein an amino functional siloxane selected from the group consisting of:

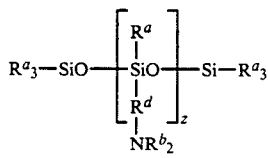

and

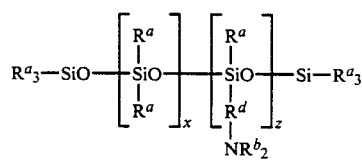

is reacted with a halogenated salt of a carboxylic acid of the general formula: $Y-R^cCOO^-Na^+$, wherein each $R^a$ is a lower alkyl group, each $R^b$ is selected from the group consisting of hydrogen or a lower alkyl group, $R^c$ is a lower alkylene group, $R^d$ is selected from the group consisting of hydrogen and a lower alkyl group, x ranges from 1-10, z ranges from 1-4, and Y is selected from the group consisting of halogens.

* * * * *